US012719302B2

(12) United States Patent
Li et al.

(10) Patent No.: US 12,719,302 B2
(45) Date of Patent: Aug. 25, 2026

(54) POWER SUPPLY APPARATUS OF CT SHELTER SYSTEM

(71) Applicant: Siemens Healthcare GmbH, Erlangen (DE)

(72) Inventors: Lin Li, Shanghai (CN); Zhen Bin Huang, Shanghai (CN); Xue Wen Zhang, Jinan (CN)

(73) Assignee: Siemens Healthineers AG, Erlangen (DE)

( * ) Notice: Subject to any disclaimer, the term of this patent is extended or adjusted under 35 U.S.C. 154(b) by 566 days.

(21) Appl. No.: 18/085,625

(22) Filed: Dec. 21, 2022

(65) Prior Publication Data

US 2023/0198292 A1 Jun. 22, 2023

(30) Foreign Application Priority Data

Dec. 21, 2021 (CN) ........................ 202123235540.2

(51) Int. Cl.
*H02J 9/06* (2006.01)
*H02P 27/06* (2006.01)
*A61B 6/03* (2006.01)

(52) U.S. Cl.
CPC .............. *H02J 9/062* (2013.01); *H02P 27/06* (2013.01); *A61B 6/03* (2013.01); *B60L 2210/30* (2013.01)

(58) Field of Classification Search
CPC ...................................................... A61B 6/035
See application file for complete search history.

(56) References Cited

U.S. PATENT DOCUMENTS

| | | | | |
|---|---|---|---|---|
| 5,827,095 A * | 10/1998 | Mantere | B63H 21/305 440/111 |
| 6,505,806 B1 * | 1/2003 | Glaesener | F16M 7/00 248/677 |
| 6,560,131 B1 * | 5/2003 | vonBrethorst | H02J 7/0042 363/146 |
| 10,790,670 B1 * | 9/2020 | Alimadad | H02J 7/34 |
| 2016/0242705 A1 * | 8/2016 | Richardson | A61B 6/56 |

* cited by examiner

*Primary Examiner* — Daniel Kessie
(74) *Attorney, Agent, or Firm* — Banner & Witcoff, Ltd.

(57) ABSTRACT

A power supply apparatus of a computerized tomography (CT) shelter system is provided. The power supply apparatus comprises a power source buffer unit and a generator. The power source buffer unit comprises a battery module and an inverter module. The battery module is used to store electric energy. The inverter module may convert low-level alternating-current power into direct-current power, which is then stored in the battery module, and may also convert the direct-current power stored in the battery module into high-level alternating-current power that is then supplied to a CT apparatus of the CT shelter system. The generator may generate the low-level alternating-current power that is then supplied to the inverter module, and the generator may also supply the generated low-level alternating-current power to an air conditioning apparatus of the CT shelter system.

11 Claims, 3 Drawing Sheets

10 Battery buffer unit
12 Battery module
14 Inverter module
20 Generator
30 External power source interface
40 Dual power switch
42 Circuit breaker
60 CT apparatus
70 Air conditioning apparatus 10 Battery buffer unit
12 Battery module
14 Inverter module
20 Generator
60 CT apparatus
70 Air conditioning apparatus 10 Battery buffer unit
12 Battery module
14 Inverter module
20 Generator
30 External power source interface
40 Dual power switch
42 Circuit breaker
60 CT apparatus
70 Air conditioning apparatus 20 Generator
50 Shelter body
52 Room
60 CT apparatus
70 Air conditioning apparatus

POWER SUPPLY APPARATUS OF CT SHELTER SYSTEM

CROSS-REFERENCE TO RELATED APPLICATIONS

The present application claims priority to and the benefit of China patent application no. CN 202123235540.2, filed on Dec. 21, 2021, the contents of which are incorporated herein by reference in its entirety.

TECHNICAL FIELD

The present disclosure relates to a power supply apparatus and, in particular, to a power supply apparatus of a computerized tomography (CT) shelter system. The present disclosure further relates to a CT shelter system having the above power supply apparatus.

BACKGROUND

A computerized tomography (CT) shelter system may encounter the situation of being unable to connect to a power source when used in remote areas, and when the CT shelter system is moving, it is necessary to ensure the continuous operation of an air conditioner to allow a CT apparatus to be in a controlled temperature and humidity environment. Therefore, current CT shelter systems are usually equipped with a high-power generator to meet the requirements of the short-term high-power consumption of the CT apparatus. The high-power generator has disadvantages of large volume, high fuel consumption, high noise, and strong vibration. The strong vibration also affects the CT imaging quality.

SUMMARY

The purpose of the present disclosure is to provide a power supply apparatus of a CT shelter system. The power supply apparatus may be equipped with a low-power generator, and has smaller volume, lower fuel consumption, lower noise, and lower vibration compared to conventional solutions.

Another purpose of the present disclosure is to provide a CT shelter system, which may be equipped with a low-power generator and has smaller volume, lower fuel consumption, lower noise, and lower vibration compared to conventional solutions.

The present disclosure provides a power supply apparatus of a CT shelter system, the power supply apparatus comprising a power source buffer unit and a generator. The power source buffer unit comprises a battery module and an inverter module. The battery module is configured to store electrical energy. The inverter module may convert low-level alternating-current power into direct-current power that is then stored in the battery module, and the inverter module may also convert the direct-current power stored in the battery module into high-level alternating-current power that is then supplied to a CT apparatus of the CT shelter system, the voltage of the low-level alternating-current power being lower than that of the high-level alternating-current power. The generator may generate the low-level alternating-current power that is then supplied to the inverter module, and the generator may also supply the generated low-level alternating-current power to an air conditioning apparatus of the CT shelter system.

In the power supply apparatus of a CT shelter system provided in accordance with the present disclosure, the power source buffer unit is provided, and the inverter module of the power source buffer unit may convert the low-level alternating-current power into the direct-current power that is then stored in the battery module, and convert the direct-current power stored in the battery module into high-level alternating-current power that is then supplied to the CT apparatus of the CT shelter system. The low-level alternating-current power generated by the generator is supplied to the air conditioning apparatus and charges the battery module, and the power stored in the battery module meets the requirement of short-term high-power consumption of the CT apparatus. The requirement on the generator is reduced via the power source buffer unit, so a small, low-power generator may be used, thereby achieving smaller volume, lower fuel consumption, lower noise, and lower vibration compared to conventional solutions.

In yet another exemplary embodiment of the power supply apparatus of a CT shelter system, the power supply apparatus further comprises an external power source interface and a dual power switch. The external power source interface is configured to provide a connection to an external power source. The dual power switch is separately connected to the external power source interface, the generator, the inverter module, and the air conditioning apparatus. The dual power switch is configured to allow the external power source interface, the inverter module, and the air conditioning apparatus to be powered on when the external power source interface is connected to a power source, and allows the generator, the inverter module, and the air conditioning apparatus to be powered on when the external power source interface is disconnected from the power source. By means of the external power source interface and the dual power switch, the external power source may be preferentially used as the power supply when possible, and the generator may be automatically switched to supply power when the external power source is disconnected.

In yet another exemplary embodiment of the power supply apparatus of a CT shelter system, circuit breakers are respectively provided between the dual power switch and the inverter module, and between the dual power switch and the air conditioning apparatus. The circuit breakers may have a circuit protection function.

In yet another exemplary embodiment of the power supply apparatus of a CT shelter system, the low-level alternating-current power is 220 V single-phase power, and the high-level alternating-current power is 380 V three-phase power.

In yet another exemplary embodiment of the power supply apparatus of the CT shelter system, the generator is a diesel generator. In this way, it is convenient for the arrangement of a fuel tank for the generator.

In yet another exemplary embodiment of the power supply apparatus of a CT shelter system, the bottom of the generator is provided with a damping device. In this way, it is possible to further reduce the effect of the vibration of the generator on the CT imaging quality.

The present disclosure provides a CT shelter system comprising a shelter body, a CT apparatus, an air conditioning apparatus, and the power supply apparatus mentioned above. The shelter body is divided into a plurality of rooms. The CT apparatus is arranged in one of the plurality of rooms. The air conditioning apparatus is arranged in the same room as the CT apparatus. The power supply apparatus is arranged in another one of the plurality of rooms. The inverter module may convert the direct-current power stored in the battery module into high-level alternating-current power that is then supplied to the CT apparatus, and the generator may supply the generated low-level alternating-current power to the air conditioning apparatus. The CT shelter system according to the present disclosure may use a small low-power generator, and thus has smaller volume, lower fuel consumption, lower noise, and lower vibration compared to conventional solutions.

BRIEF DESCRIPTION OF THE DRAWINGS

The accompanying drawings below illustrate and explain the present disclosure, without limiting the scope thereof.

KEY TO LABELS

Figure 1:
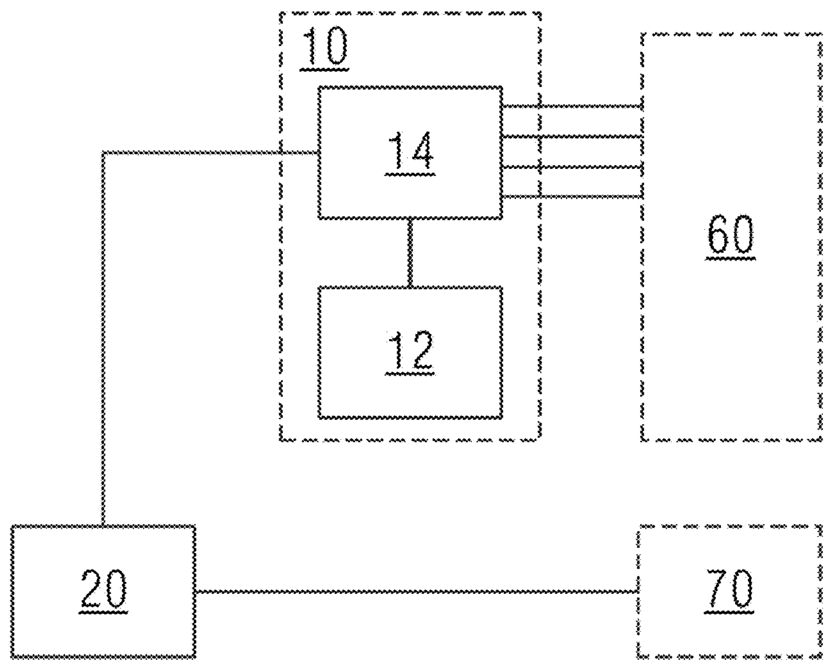
FIG. 1 is a schematic structural diagram of an exemplary embodiment of a power supply apparatus of a CT shelter system, in accordance with the disclosure.

10 Battery buffer unit
12 Battery module
14 Inverter module
20 Generator
30 External power source interface
40 Dual power switch
42 Circuit breaker
50 Shelter body
52 Room
60 CT apparatus
70 Air conditioning apparatus

DETAILED DESCRIPTION OF THE DISCLOSURE

To enable a clearer understanding of the technical features, objectives, and effects of the disclosure, particular embodiments are now explained with reference to the accompanying drawings, in which identical labels indicate structurally identical components or components with similar structures but identical functions.

The term "exemplary" herein means "serving as an example, instance or description," and any "exemplary" illustration and embodiment herein should not be interpreted as a more preferred or a more advantageous technical solution.

To make the drawings appear uncluttered, only those parts relevant to the present utility model are shown schematically in the drawings; they do not represent the actual structure thereof as a product.

FIG. 1 is a schematic structural diagram of an exemplary embodiment of a power supply apparatus of a CT shelter system. Referring to FIG. 1, the power supply apparatus of a CT shelter system comprises a power source buffer unit 10 and a generator 20.

The power source buffer unit 10 comprises a battery module 12 and an inverter module 14. The battery module 12 is configured to store electrical energy, and has a capacity according to the actual demand of the CT apparatus 60. The battery module 12 is configured to meet the requirements of short-term high-power consumption of the CT apparatus 60. The inverter module 14 is configured to convert low-level alternating-current power into direct-current power, which is then stored in the battery module 12. The inverter module 14 is configured to convert the direct-current power stored in the battery module 12 into high-level alternating-current power, which is then supplied to the CT apparatus 60 of the CT shelter system, the voltage of the low-level alternating-current power being lower than that of the high-level alternating-current power. In the exemplary embodiment, the low-level alternating-current power is 220 V single-phase power, and the high-level alternating-current power is 380 V three-phase power. However, it is not limited thereto, and in another exemplary embodiment, the low-level alternating-current power and the high-level alternating-current power may be any suitable values that are provided according to the actual implementation and power consumption requirements of the CT apparatus 60.

The generator 20 may generate the low-level alternating-current power, which is then supplied to the inverter module 14, and the generator 20 may also supply the generated low-level alternating-current power to an air conditioning apparatus 70 of the CT shelter system. In the exemplary embodiment, the generator 20 is a 10 kW "small" generator with a 220 V single-phase output. Compared with a large generator with a 380 V three-phase output, the small generator has a smaller volume, lower fuel consumption, lower noise, and lower vibration.

In the power supply apparatus of a CT shelter system provided in the present disclosure, the power source buffer unit 10 is provided, and the inverter module 14 of the power source buffer unit is configured to convert the low-level alternating-current power into the direct-current power, which is then stored in the battery module 12, and is also configured to convert the direct-current power stored in the battery module 12 into high-level alternating-current power, which is then supplied to the CT apparatus 60 of the CT shelter system. The low-level alternating-current power generated by the generator 20 is supplied to the air conditioning apparatus 70, and charges the battery module 12. The CT apparatus 60 only requires high-power consumption during an exposure stage, and otherwise has low-power consumption requirements. The electrical energy stored in the battery module 12 meets the requirement of this short-term high-power consumption of the CT apparatus 60, and is charged when the power of the CT apparatus 60 is low, to be ready for the next high-power consumption of the CT apparatus 60. The requirement of the generator is reduced via the power source buffer unit 10, such that a small low-power generator may be used, thereby achieving smaller volume, lower fuel consumption, lower noise, and lower vibration compared to conventional solutions.

Figure 2:
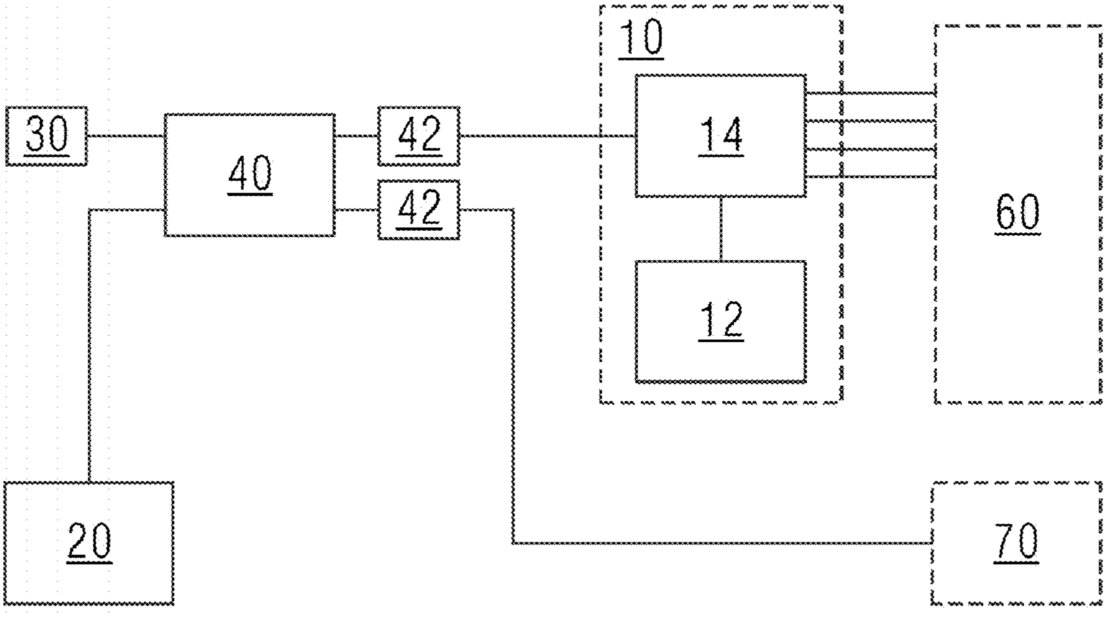
FIG. 2 is a schematic structural diagram of another exemplary embodiment of the power supply apparatus of a CT shelter system, in accordance with the disclosure.

FIG. 2 is a schematic structural diagram of another exemplary embodiment of the power supply apparatus of a CT shelter system. Referring to FIG. 2, the parts of the power supply apparatus the same as or similar to those in FIG. 1 will not be repeated, as the difference lies in that the power supply apparatus further comprises an external power source interface 30 and a dual power switch 40. The external power source interface 30 is used for connection to an external power source. The dual power switch 40 is separately connected to the external power source interface 30, the generator 20, the inverter module 14, and the air conditioning apparatus 70. The dual power switch 40 enables the external power source interface 30, the inverter module 14, and the air conditioning apparatus 70 to be powered on when the external power source interface 30 is connected to a power source, and enables the generator 20, the inverter module 14, and the air conditioning apparatus 70 to be powered on when the external power source interface 30 is disconnected from the power source. Via the external power source interface 30 and the dual power switch 40, the external power source may be preferentially used for power supply when possible, and the generator 20 may be automatically switched to supply power when the external power source is disconnected.

In the exemplary embodiment, referring to FIG. 2, circuit breakers 42 are respectively provided between the dual power switch 40 and the inverter module 14, and between the dual power switch 40 and the air conditioning apparatus 70. The circuit breakers 42 conveniently control a circuit, and may also protect the circuit when overloaded, short-circuited, when an undervoltage condition is present, etc. within the circuit.

In the exemplary embodiment, the generator 20 is a diesel generator. A vehicle typically used to drive the CT shelter system uses a diesel engine. The generator 20 using a diesel generator may thus share a common fuel tank with an engine of the vehicle, and as a result provides a convenient solution in that the vehicle and generator share the same type of fuel.

In the exemplary embodiment, the bottom of the generator 20 is provided with any suitable type of damping device, such as a rubber damper pad, a spring damper, a hydraulic damper, etc. In this way, it is possible to further reduce the effects of the vibration of the generator 20 on the CT imaging quality.

Figure 3:
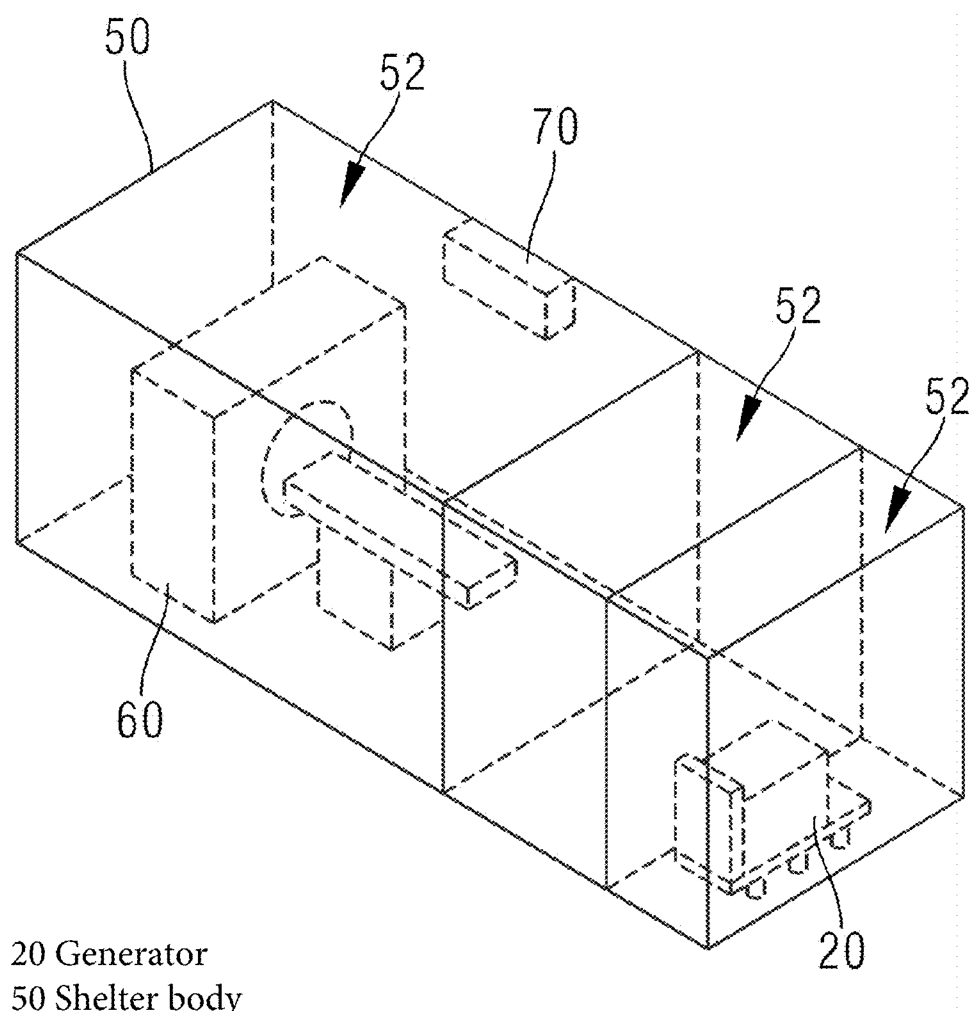
FIG. 3 is a schematic structural diagram of an exemplary embodiment of a CT shelter system, in accordance with the disclosure.

The present disclosure provides a CT shelter system. FIG. 3 is a schematic structural diagram of an exemplary embodiment of a CT shelter system. Referring to FIG. 3, the CT shelter system comprises a shelter body 50, a CT apparatus 60, an air conditioning apparatus 70, and a power supply apparatus mentioned above. The shelter body 50 is divided into a plurality of rooms 52. The CT apparatus 60 is arranged in one room 52 among the plurality of rooms 52. The air conditioning apparatus 70 is arranged in the same room 52 as the CT apparatus 60, and may control the temperature and humidity of the environment where the CT apparatus 60 is located. The power supply apparatus is arranged in another room 52 among the plurality of rooms 52. The inverter module 14 may convert the direct-current power stored in the battery module 12 into high-level alternating-current power, which is then supplied to the CT apparatus 60. The generator 20 is configured to supply the generated low-level alternating-current power to the air conditioning apparatus 70. The CT shelter system according to the present disclosure may use a small low-power generator, and thus has smaller volume, lower fuel consumption, lower noise, and lower vibration compared to conventional solutions.

It should be understood that although the description herein is based on various embodiments, it is by no means the case that each embodiment contains just one independent technical solution. Such a method of presentation is adopted herein purely for the sake of clarity. Those skilled in the art should consider the description in its entirety. The technical solutions in the various embodiments could also be suitably combined to form other embodiments understandable to those skilled in the art.

The foregoing detailed description is merely a specific description directed to the feasible embodiments of the present disclosure, and are not intended to limit the scope of protection of the present disclosure, and any equivalent embodiment or alteration, such as the combination, segmentation or duplication of features made without departing from the technical spirit of the present disclosure should be included within the scope of protection thereof.

The various components described herein may be referred to as "units" or "modules." Such components may be implemented via any suitable combination of hardware and/or software components as applicable and/or known to achieve the intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer readable medium. Regardless of the particular implementation, such units and modules, as applicable and relevant, may alternatively be referred to herein as "circuitry," "processors," or "processing circuitry," or alternatively as noted herein.

What is claimed is:

1. A power supply of a computerized tomography (CT) shelter system, comprising:

a battery configured to store electrical energy;

a power converter configured to (i) convert first alternating-current (AC) power into direct-current (DC) power to charge the battery during operation of a CT apparatus of the CT shelter system in non-exposure stages in which the CT apparatus operates in accordance with a first level of power consumption, and (ii) convert the DC power stored in the battery to second AC power that is supplied to the CT apparatus during operation of the CT apparatus in an exposure stage in which the CT apparatus operates in accordance with a second level of power consumption, wherein the first level of power consumption is less than the second level of power consumption, wherein the first AC power comprises single-phase power, and the second AC power comprises three-phase power, a voltage that is-identified with the first AC power being lower than a voltage identified with the second AC power;

a generator configured to generate the first AC power, which is supplied to the power converter and to an air conditioning apparatus of the CT shelter system;

an external power source interface configured to connect to an external power source; and a dual power switch connected to the external power source interface, the generator, the power converter, and the air conditioning apparatus, wherein the dual power switch is configured (i) to allow the external power source interface, the power converter, and the air conditioning apparatus to be powered on when the external power source interface is connected to the external power source, and (ii) to allow the generator, the power converter, and the air conditioning apparatus to be powered on when the external power source interface is disconnected from the external power source.

2. The power supply of claim 1, further comprising:

a first circuit breaker coupled to the dual power switch and to the power converter; and a second circuit breaker coupled to the dual power switch and to the air conditioning apparatus.

3. The power supply of claim 1, wherein the first AC power comprises 220 V single-phase power, and wherein the second AC power comprises 380 V three-phase power.

4. The power supply of claim 1, wherein the generator comprises a diesel generator.

5. The power supply of claim 1, further comprising:

a damping device coupled to a bottom of the generator.

6. The power supply of claim 5, wherein the damping device comprises a rubber damper pad, a spring damper, or a hydraulic damper.

7. A computerized tomography (CT) shelter system, comprising:

a shelter body comprising a plurality of rooms;

a CT apparatus disposed in a first room from among the plurality of rooms;

an air conditioning apparatus disposed in the first room; and a power supply apparatus disposed in a second room from among the plurality of rooms, the power supply apparatus comprising:

a battery configured to store electrical energy;

a power converter configured to (i) convert first alternating-current (AC) power into direct-current (DC) power to charge the battery during operation of the CT apparatus in non-exposure stages in which the CT apparatus operates in accordance with a first level of power consumption, and (ii) convert the DC power stored in the battery to second AC power that is supplied to the CT apparatus during operation of the CT apparatus in an exposure stage in which the CT apparatus operates in accordance with a second level of power consumption, wherein the first level of power consumption is less than the second level of power consumption, wherein the first AC power comprises single-phase power, and the second AC power comprises three-phase power, a voltage that is identified with the first AC power being lower than a voltage identified with the second AC power;

a generator configured to generate the first AC power, which is supplied to the power converter and to the air conditioning apparatus;

an external power source interface configured to connect to an external power source; and a dual power switch connected to the external power source interface, the generator, the power converter, and the air conditioning apparatus, wherein the dual power switch is configured (i) to allow the external power source interface, the power converter, and the air conditioning apparatus to be powered on when the external power source interface is connected to the external power source, and (ii) to allow the generator, the power converter, and the air conditioning apparatus to be powered on when the external power source interface is disconnected from the external power source.

8. The power supply of claim 1, wherein the dual power switch is separate from the power converter.

9. The power supply of claim 8, further comprising:

a first circuit breaker coupled to the dual power switch and to the power converter.

10. The power supply of claim 1, wherein the dual power switch is configured to automatically switch the generator to supply power when the external power source is disconnected from the external power source interface.

11. The power supply of claim 1, wherein the dual power switch is separately connected to the external power source interface, the generator, the power converter, and the air conditioning apparatus.

* * * * *